(12) United States Patent
Zimmermann

(10) Patent No.: US 7,157,257 B2
(45) Date of Patent: Jan. 2, 2007

(54) METHOD OF TREATING BIOLOGICAL CELLS AND/OR THEIR CELL COMPONENTS WITH ELECTRICAL FIELDS

(75) Inventor: Ulrich Zimmermann, Waldbrunn (DE)

(73) Assignee: Eppendorf AG, Hamburg (DE)

( * ) Notice: Subject to any disclaimer, the term of this patent is extended or adjusted under 35 U.S.C. 154(b) by 636 days.

(21) Appl. No.: 10/348,831

(22) Filed: Jan. 22, 2003

(65) Prior Publication Data

US 2003/0138924 A1 Jul. 24, 2003

(30) Foreign Application Priority Data

Jan. 24, 2002 (DE) ................ 102 02 709

(51) Int. Cl.
*C12N 13/00* (2006.01)
*C12N 9/50* (2006.01)

(52) U.S. Cl. ............... 435/173.1; 435/70.2; 435/70.21; 435/173.4; 435/173.5; 435/173.6; 435/173.9; 435/184; 435/212; 435/219; 435/346; 436/548

(58) Field of Classification Search ............... 435/70.2, 435/70.21, 173.1, 173.4, 173.5, 173.6, 173.9, 435/184, 212, 219, 346; 436/548
See application file for complete search history.

(56) References Cited

U.S. PATENT DOCUMENTS 4,578,167 A * 3/1986 Schoner ..................... 435/450
5,403,585 A * 4/1995 Malfroy-Camine et al. ...... 424/94.67

OTHER PUBLICATIONS

G. Fuhr, U. Zimmermann and S. G. Shirley, "Electromanipulation of Cells," Cell Motion in Time-Varying Fields: Principles and Potential, Chapter 5, pp. 259-328, CRC Press, Buca Raton, 1996.
U. Zimmermann and C. Pilwat "Electric Field Simulated Fusion: Increased Field Stability of Cells Induced by Pronase," Naturwissenschaften 68, p. 577, Springer Verlag, 1981.

* cited by examiner

*Primary Examiner*—David Saunders
(74) *Attorney, Agent, or Firm*—Robert A. Koons, Jr.; Matthew P. McWilliams; Drinker, Biddle & Reath LLP

(57) ABSTRACT

A method is described for treating biological cells and/or their cell components with electrical fields in a reaction medium, in which an inhibitor is added to the reaction medium to counteract the action of enzymes that break down protein.

14 Claims, 1 Drawing Sheet

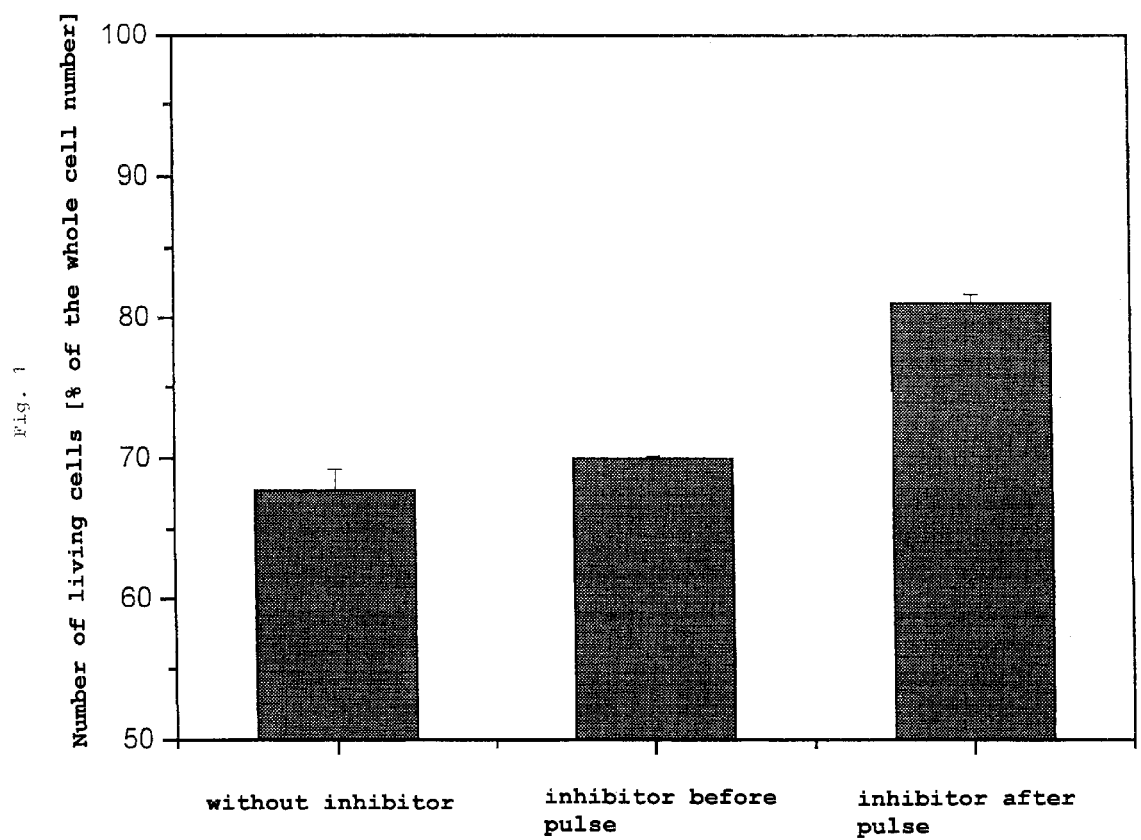

METHOD OF TREATING BIOLOGICAL CELLS AND/OR THEIR CELL COMPONENTS WITH ELECTRICAL FIELDS

FIELD OF THE INVENTION

The present invention relates to a method of treating biological cells and/or their cell components with electrical fields in a reaction medium.

TECHNOLOGICAL BACKGROUND

A number of methods are already known for treating membranes of biological cells and/or their cell components by way of exchanging biological material between them. In recent years various methods of transmitting biological material through the membrane of a cell have increasingly gained in importance. In this method, membrane-impermeable molecules are sluiced through pores which have been formed in the membrane through external forces.

It is known to treat cell membranes with chemical substances to make them permeable. In particular these include pore-forming and/or diffusion-promoting compounds. In this context peptide antibiotics, such as valinomycin, and detergents such as sodium dodecylsulphate or triton X-100 can be used.

Another possibility of making the membranes of biological cells permeable is electrical permeabilisation. This includes methods such as electrotransfection, electroporation and electrofusion. These methods are carried out in macroscopic devices as well as in Microsystems or microstructures.

Electrical permeabilisation has the advantage that it can be implemented without a vehicle and without externally added chemicals. Electropermeabilisation by means of an electrical field, also known as "electroporation", has for some time been an established method of taking up free DNA in, for example, eukaryotic cells. This is done by exposing the eukaryotic cells to an electrical field with high field strength in the presence of DNA. It is presumed that as a result of the "electric shock" pores are temporarily formed in the membrane. This allows the DNA to be transmitted and to flow into a biological cell (Zimmermann and Neil, 1996 [Zimmerman, U. and Neil G. A. (Eds)][1996] Electromanipulation of Cells, CRC Press, Boca Raton).

In practice it has been found that often not necessarily all of the biological cells are influenced by the electrical field in the same way. In particular in the case of the fusion of smaller and larger cells the problem arises that in general the large cells are destroyed as the critical field strength for these cells is less than for small ones (integrated Laplace equation) (Zimmermann and Neil; citation see above). During the destruction of the cells, i.e. when the membrane bursts, proteolytic enzymes are released which can modify the membrane proteins of the intact and/or fused cells. This is associated with considerable drawbacks. The released proteolytic enzymes affect the fused cells products to the extent that they cannot carry out the intended function. This becomes a major problem especially if, for example, allogenic dendritic cells have been treated in the electrical field and the resulting products of fusion have been so modified in their membrane structure that they do no produce the desired immune response after injection into the patient. Similar problems can occur during the production of hybridoma cells through the electrofusion of B-lymphocyte cells with myeloma cells. Thus it has been observed that due to the destruction of cells in the electrical field, proteolytic cells are present in the medium which negatively affect the hybridome clones produced during electrofusion.

OBJECT OF THE INVENTION

It is therefore the object of the present invention to provide a method of treating biological cells in an electrical field, with which it is possible, despite the presence of interfering proteins, to produce cell fusion products exhibiting the desired effect.

SUMMARY OF THE INVENTION

The present invention relates to a method of treating biological cells and/or their cell components with electrical fields in a reaction medium, which is characterised in that an inhibitor against the effect of enzymes that break down proteins is added to the reaction medium.

The subclaims define preferred embodiments of the method according to the invention.

In accordance with the invention it has been found that enzymes that break down proteins that are contained in the reaction medium can be rendered harmless if an inhibitor substance is added to the reaction medium. The proteolytic enzymes produced as a result of the destruction of the large cells in the electrical field are inactivated (and/or bound) through the action of the inhibitor with the consequence that excellent fusion results in term of the quality and quantity of the fused cells can be achieved.

Enzymes that break down protein can, for example, be enzymes that break down the protein components of the cell membrane. Furthermore, proteins can also be involved, which intracellularly do not occur membrane-bound.

PREFERRED EMBODIMENTS OF THE INVENTION

The present invention is explained with reference to FIG. 1. FIG. 1 shows a block diagram from which it can be seen that by adding the inhibitor to the reaction medium, the living cell number can be considerably increased if an inhibitor is present in the reaction medium.

The inhibitor can be a protease inhibitor or a mixture of at least two protease inhibitors. In a preferred embodiment a mixture of four to six protease inhibitors is used.

Preferably, the protease inhibitors are specifically adapted for inhibition of proteases involved in the destruction of the cell membranes. These include, for example, aspartate proteases, cysteine proteases, serine proteases, metalloproteases and/or aminopeptidases.

In a preferred embodiment of the method in accordance with the invention, commercially available protease inhibitors mixtures ("protease inhibitor cocktails") are beneficially used. This has the advantage that precisely these mixtures are well-matched and therefore develop the required action. However, it is also easily possible to produce a particular mixture on an individual basis.

The method in accordance with the invention can be implemented with good results if the inhibitor is used in a concentration range of 1 ng/ml to 1 mg/ml.

In an alternative embodiment of the method according to the invention, a specific antibody or a mixture of at least two specific antibodies can be used as the inhibitor. If required, special antibodies against the action of enzyme-degrading proteins can be cultivated. However, commercially available antibodies can also be used.

The antibody/antibodies is/are immobilised, i.e. it/they are immobilised on a carrier material, or bonded to it and added with the carrier material to the cell suspension. After binding the proteases to the antibodies the carrier material, including the protease-antibody complex, can be easily removed.

The biological cells to be treated in an electrical field are not subject to any particular restrictions, with the proviso that they can be treated, fused for example, in the electrical field. Prokaryotic or eukaryotic cells, including plant cells in the form of protoplasts, can be used as biological cells for example. It is also possible to treat cell components in an electrical field. Depending on the intended use of the fused cells they can be genetically modified.

Examples of eukaryotic cells are antigen-presenting cells and tumour cells. The antigen-presenting cells can be allogenic or autologous.

Preferred antigen-presenting cells are dendritic cells. These are able to present the antigens so that they are recognised by the T-cells. The dendritic cells act as immunoactive cells, which have immunostimulating properties depending on the antigens in question. Dendritic cells modified with antigens are structured in such a way that the antigens are incorporated in processed form into the surface of the dendritic cell.

Other examples of eukaryotic cells are B-lymphocytes and myeloma cells. These cells are fused forming hybridoma clones which secrete antibodies.

As has been stated above, modification of the biological cells takes place in the electrical field. These modifications are generally cell fusions. These fusions are, for example, carried out by way of dielectrophoresis and subsequent fusion through electroporation.

Dielectrophoresis and electroporation are already established processes. With regard to these reference is made to Zimmermann and Neil (citation see above). The components of the pulse medium, the pulse duration and the strength of the electrical field are generally specific to the cells to the treated.

Modification is preferably carried out in a suspension. The suspended cells are exposed to the aforementioned electrical field in the suspension in such a way that the different cell types or cell components attract each other. Coming into contact under the influence of the electrical field is sufficient to exclusively transfer certain components from one cell to another. For example, only membrane components with antigens of diseased cells or cell components are transferred to dendritic cells.

In general, in terms of timing there are two possibilities of adding the inhibitor to the reaction medium. One possibility is adding the inhibitors to the reaction medium before applying the electrical field. It has been found that with this procedure the living cell number can be considerably increased.

Alternatively the inhibitor can be added to the reaction medium after applying the electrical field. Preferably the inhibitor is added when resealing has already been carried out. In this form of embodiment in particular, it has been found that the living cell number can be considerably increased, indeed much more sharply than in the previous embodiment.

Reference is made to FIG. 1 in connection with this. The shown block diagram illustrates experiments in which the living cell number (in %) was studied in suspensions with inhibitor, with inhibitor before pulse application or with inhibitor after pulse application, respectively. It can clearly be seen that the number of living cells can be increased if an inhibitor is added to the pulse medium. An increase can already be seen if the inhibitor is added before pulse application, but far better results are obtained if the inhibitor is added after pulse application.

After treating the reaction medium with the inhibitor, the latter must be separated in order to avoid any possible disturbance by the inhibitors. Thus, for example, the inhibitor must be separated before re-injection into the patient. Separation takes place by way of usual prior art methods. As a rule, separation takes place through washing the cells two to three times with an inhibitor-free medium. Moreover, the inhibitor can be inactivated, for example through changing the pH value.

According to the present invention an adaptation of the average cell diameter of the fusion partners also takes place through the treatment with electrical field pulses. The adaptation of the cell sizes (the large cells are destroyed) of the fusion partners result in better fusion yields.

The following example serves for further explanation of the method in accordance with the invention in more detail.

EXAMPLE

Electropermeabilisation of eukaryotic suspension cells in the presence of protease inhibitors in the medium.

Cell line Sp2/0-Ag14 (mouse myeloma cells) was used as the biological cells. These cells were transferred into Pora 25 hypoporation medium (25 mM KCl, 1.2 mM phosphate buffer, pH 7.4 adjusted to 150 mosmol with inosite). Protease inhibitor cocktail set III (Calbiochem, catalogue no. 539132) was used as the protease inhibitor. The dilution of the inhibitor in the pulse medium was 1:100. The pulse conditions for permeabilisation were 2 kV/cm, 100 µs.

The Sp2 cells were centrifuged out of a current cell culture (200 g, 10 mins). They were then washed once in PBS and once in poration medium. The cells were then incorporated into poration medium up to a concentration of $1\times10^6$ cell/ml.

Three batches were prepared:
1. As a reference sample Sp2 cells were added to the poration medium, followed by pulse application.
2. The Sp2 cells were added to the poration medium together with the protease inhibitor cocktail, followed by pulse application.
3. The Sp2 cells were added to the poration medium, followed by pulse application. Subsequently a resealing has been taken place, after which the inhibitor cocktail was added.

Control cells were also treated in the same way, but without pulse application.

Resealing took place in the pulse cuvette within 10 minutes at room temperature. The cell suspension was transferred from the pulse cuvette into 5 ml CGM (complete growth medium) without phenol red. The cells were then incubated for one hour in the gas chamber with 5% $CO_2$ at 37° C. The cells from each of the three batches as well as the corresponding control cells were then electronically measured in the CASY-1. A graphic representation of the results as a percentage of the living cells after pulse application in relation to the unpulsed control cells is shown in FIG. 1. Evaluation took place with the Origin 5.0® software.

I claim:

1. A method of treating biological cells or components of biological cells with electrical fields in a reaction medium comprising, providing a suspension in a reaction medium, the suspension comprising biological cells, components of biological cells, or a mixture thereof, wherein an inhibitor to counteract an action of enzymes that break down proteins is added to the reaction medium, treating said biological cells, components of biological cells, or mixture thereof with an electrical field, and removing or inactivating the inhibitor after the treatment.

2. The method according to claim 1, wherein said inhibitor comprises a protease inhibitor or a mixture of at least two protease inhibitors.

3. The method according to claim 2, wherein said protease inhibitor or mixture of protease inhibitors is specifically adapted for inhibiting aspartate proteases, cysteine proteases, seine proteases, metallo-proteases and/or aminopetidases.

4. The method according to any one of claims 1 to 3, wherein said inhibitor is added in a concentration of 1 ng/ml to 1 mg/ml.

5. The method according to claim 1, wherein said inhibitor comprises an antibody or a mixture of at least two antibodies specific against proteolytic enzymes released by the destruction of biological cells on exposure to the electrical field.

6. The method according to claim 5, wherein said antibody or mixture of antibodies is immobilized on a carrier material.

7. The method according to claim 1, wherein said biological cells comprise prokaryotic cells, eukaryotic cells or plant cells in the form of protoplasts.

8. The method according to claim 7, wherein said prokaryotic cells, eukaryotic cells or plant cells are genetically modified.

9. The method according to claim 7 or 8, wherein said eukaryotic cells comprise antigen-presenting cells, tumor cells, B-lymphocytes or myeloma cells.

10. The method according to claim 1, further comprising fusing the biological cells in the electrical field.

11. The method according to claim 10, wherein the fusion comprises dielectrophoresis and electroporation.

12. The method according to claim 1, wherein the inhibitor is added to the reaction medium before the electrical field is applied.

13. The method according to claim 1, wherein the inhibitor is added to the reaction medium after the electrical field is applied.

14. The method according to claim 1, wherein the inhibitor is removed by washing the cells at least two times in an inhibitor-free medium.

* * * * *